United States Patent [19]

Funatsu

[11] Patent Number: 4,602,631
[45] Date of Patent: Jul. 29, 1986

[54] FORCEPS FOR CLAMPING SURGICAL CLIPS

[76] Inventor: Noboru Funatsu, Act III No. 1008, 15-4, Doyama-cho, Kita-ku, Osaka, Japan

[21] Appl. No.: 601,844

[22] Filed: Apr. 19, 1984

[30] Foreign Application Priority Data

Sep. 8, 1983 [JP] Japan .................................. 58-166340
Sep. 27, 1983 [JP] Japan .................................. 58-181703

[51] Int. Cl.$^4$ .............................................. A61B 17/12
[52] U.S. Cl. ...................................... 128/321; 128/325
[58] Field of Search ................ 128/326, 325, 321, 322

[56] References Cited

U.S. PATENT DOCUMENTS

| 1,496,132 | 6/1924 | Rombough | 128/321 |
| 3,828,791 | 8/1974 | Santos | 128/321 |
| 3,954,108 | 5/1976 | Davis | 128/325 |

Primary Examiner—Jay N. Eskovitz
Attorney, Agent, or Firm—Wenderoth, Lind & Ponack

[57] ABSTRACT

A surgical clip has projections on its load-bearing portion. Also, a forceps used with the surgical clip is formed with depressions or small holes to receive the projections on the surgical clip.

1 Claim, 31 Drawing Figures

FORCEPS FOR CLAMPING SURGICAL CLIPS

BACKGROUND OF THE INVENTION

1. Field of the Invention

The present invention relates to a surgical clip and forceps for clamping the same.

2. Description of the Prior Art

The microdissection of an aneurism is one of the high-grade operations which have been made possible by a recent advance of surgical technique. However, it is such a difficult operation as to require the greatest possible care and a high technical skill, because the patient is exposed to the danger of excessive bleeding which may becaused by the rupture of the aneurism during the operation. Moreover, stenosis or obstruction of an artery or a capillary vessel in the proximity thereof must not be caused by the clamping of the aneurism. Because of these requirements, it is most common to perform an operation for an aneurism under a microscope of 6 to 20 magnifications. From such minuteness required for performing the operation, various restrictions imposed on the operative instruments are derived.

Conventional clips and forceps pose the following problems:

1. In spite of various shapes and dimensions in which conventional clips are available, conventional forceps do not always allow these clips to be directed in a desired direction according to the position of the aneurism. Consequently, it is sometimes entirely impossible to clamp an aneurism.

2. The thick-bodied end portions of conventional forceps interfere with the visual field to a great degree.

3. A surgeon cannot operate conventional forceps with certainty when the direction in which the two jaws of the forceps have to be moved toward one another for clamping an aneurism differs with the aptitude of his hand. Consequently, it is sometimes impossible to assure the safety of the patient in clamping an aneurism.

Conventional clips widely used by surgeons, especially by brain surgeons, for the arrest of bleeding from an aneurism or a blood vessel or for the treatment of blood vessel obstruction are divided broadly into two groups, one of which includes clips made by bending or curving slender metal wires as shown in FIGS. 1 to 6, while the other includes clips made of long and narrow metal plates as shown in FIG. 7. Conventional clips can also be divided in another way on the basis of structural differences according to the order in which three portions of a clip are arranged: i.e. either a spring eye (or fulcrum) 2, a load-bearing portion 3 and a clamping jaw portion 1 or the load-bearing portion 3, the spring eye 2 and the clamping jaw portion 1. As for the shapes of conventional clips, there are scores of kinds of shapes in addition to those shown in FIGS. 1 to 7. For example, clips having arc-shaped, L-shaped, J-shaped or bayonet-shaped bends are full of variety in dimensions and angles of bend, and are curved or bent in parallel with or perpendicularly to the direction in which the gripping power is applied to the load-bearing portion 3.

Some conventional forceps such as Sugita's, Sano's and FM forceps are used specially to operate the abovedescribed clips in a confined space. As shown in Figs. 8 to 10, a forceps has a holding portion 4, connecting portion (or fulcrum) 5 and grip portion 6. Two jaws constituting the holding portion 4 engage the load-bearing portion 3 of a clip, which is pressed so as to open the clamping jaw portion 1 when the grip portion 6 is clasped. When the surgeon relaxes his hand, the clamping jaw portion 1 of thelip is closed. The clip gets clear of the holding portion 4 when the surgeon further relaxes his hand so as to open the grip portion 6.

In case of a forceps shown in FIG. 8 or 10, two levers constituting the grip portion 6 bear resemblance to tweezers and are connected with each other by a leaf spring. When a pair of binding metals 7 provided on the inside opposite surfaces of these two levers are allowed to engage each other, the clip is left gripped with the clamping jaw portion 1 kept open. In case of a forceps shown in FIG. 9, the levers are provided with rings to be passed over a thumb and a forefinger. When the levers are moved toward or away from each other, a mechanism extending from the connecting portion to the holding portion 4 transmits the movement of the levers to one or both of the jaws constituting the holding portion 4 and opens or closes the holding portion 4.

In case of a forceps shown in FIG. 8, 10, 11 or 12, grooves 4' are provided in the inside opposite surfaces of the end portions of the jaws constituting the holding portion 4. The shape of the grooves 4' is substantially complementary to the curvature of the load-bearing portion 3 of a clip. With this type of forceps, however, the clip can be directed only in a sense which is determined by the direction of the grooves 4'. In order to eliminate this drawback, several types of forceps including two types of Sano's forceps have already been developed. One type of Sano's forceps can be bent both in the holding portion 4 and in the grip portion 6 as shown in FIG. 15 so that the direction of the clip can be adjusted to the position of an aneurism. The other type of Sano's forceps (not shown) can be bent only in the grip portion 6, while rotors 4" are provided in the holding portion 4. However, Sano's forceps, especially the former type thereof, has the disadvantages that the thick-bodied end portion interferes with the visual field in an operation performed under a microscope of 6 to 20 magnifications and that it is difficult to subject the sense of the clip to fine adjustment. In order to cover up these disadvantages, surgeons are required to keep a large number of variously shaped clips and forceps ready for their hands.

In case of a forceps shown in FIG. 9, 13 or 14, rotors 4" provided on the inside opposite surfaces of the end portions of the jaws constituting the holding portion 4 have a U-shaped section so as to adapt themselves for supporting a clip in such a manner that the load-bearing portion 3 of the clip is flanked on both sides by the legs of each rotor 4". Although this forceps is much better than the one shown in FIG. 8, 10, 11 or 12 in that the clip can be directed in any sense, the provision of the rotors 4" makes the holding portion 4 more bulky and causes a grave hindrance to the performance of an operation because of an obstructed visual field. Another trouble is that, when a clip is to be removed from an aneurism, the sense of the rotors 4" has to be mated with the direction in which the clip has been clamping the aneurism. This is troublesome all the more because each rotor 4" constituting a pair rotates separately. When an emergency such as the rupture of an aneurism occurs during an operation, several seconds required for this troublesome mating procedure may possibly cause a delay in clamping an artery and thereby lead to an irrevocable result.

Still another trouble is derived from a mechanism common to all the conventional forceps. Although they are different from one another in the shape of the grip portion 6 as shown in FIGS. 8 to 10, all of them have the same mechanism in that the movement of the grip portion 6 is transmitted to the holding portion 4 through the connecting portion (or fulcrum) 5. Therefore, when a clip is gripped by one of these conventional forceps, two jaws constituting the clamping jaw portion 1 of the clip move toward and away from one another in the direction parallel with the movement of two levers constituting the grip portion 6. When an aneurism is found on an artery running lengthwise in a field of operation, the clamping jaw portion 1 of the clip to be positioned on the neck of this aneurism has to be opened in the direction parallel with the artery and, for this purpose, two levers constituting the grip portion 6 of the forceps have to be moved in the lengthwise direction in the field of operation.

SUMMARY OF THE INVENTION

It is an object of the present invention to provide a forceps having a less bulky holding portion which may take various angles and shapes and being adapted to easily and securely grip a surgical clip and change the direction thereof.

It is another object of the present invention to provide a surgical clip having projections on the outer sides of the load-bearing portion thereof.

It is still another object of the present invention to provide a forceps in which depressions or small holes for receiving the projections of the clip are provided in the end portions of jaws constituting the holding portion.

According to the present invention, a pair of control levers constituting the above-described grip portion 6 are connected to one end of a guide tube and are joined by a pair of links which are joined together at a knee. One end of a wire rod extending through the guide tube is connected to the knee. A clamping piece is provided on the end of the wire rod projecting from the end of the guide tube. Another clamping piece is provided on the end of the guide tube. The above-described depressions or small holes for receiving the projections of the clip are provided in these clamping pieces.

With the above-described objects in view and as will become apparent from the following detailed description, the present invention will be more clearly understood in connection with the accompanying drawings.

Figure 11:
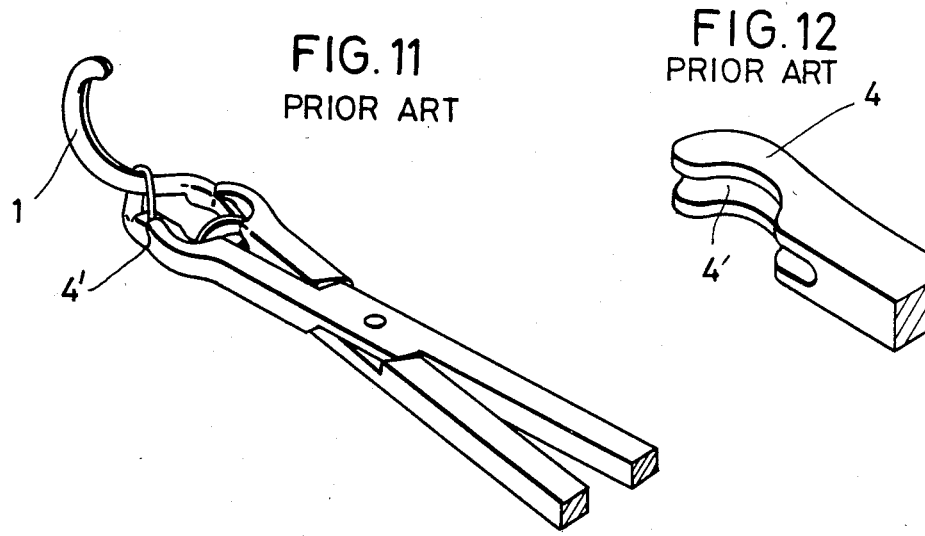
Figure 12:
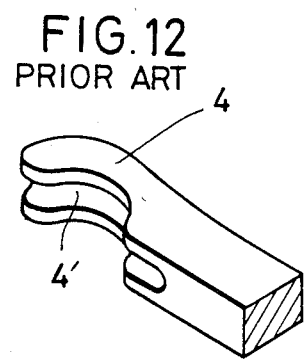
Figure 13:
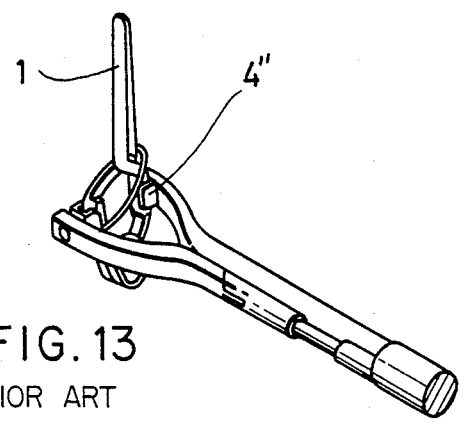
Figure 14:
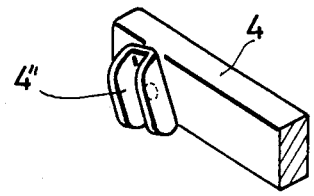
Figure 15:
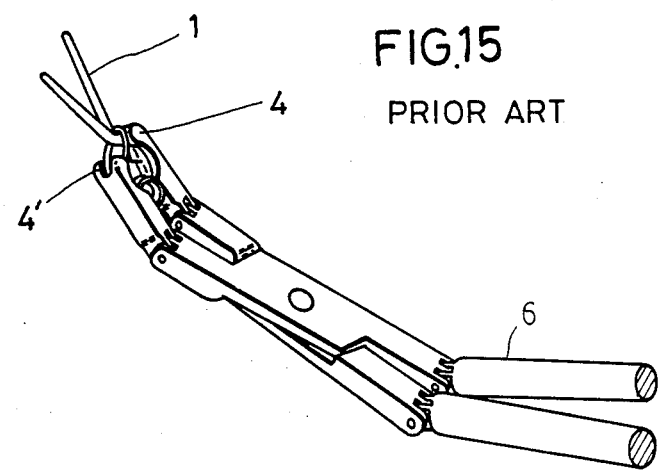
Figure 16:
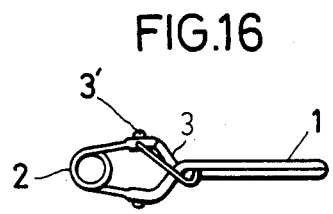
Figure 17:
Figure 18:
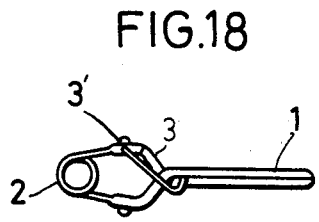
Figure 19:
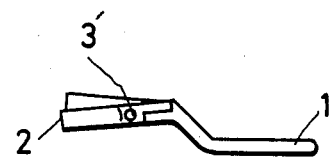
Figure 20:
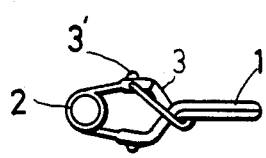
Figure 22:
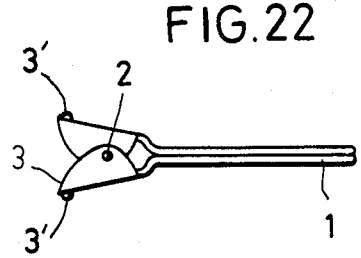
Figure 21:
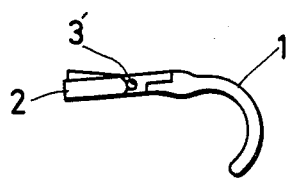
Figure 24:
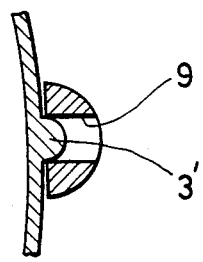
Figure 23:
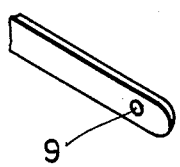
Figure 25:
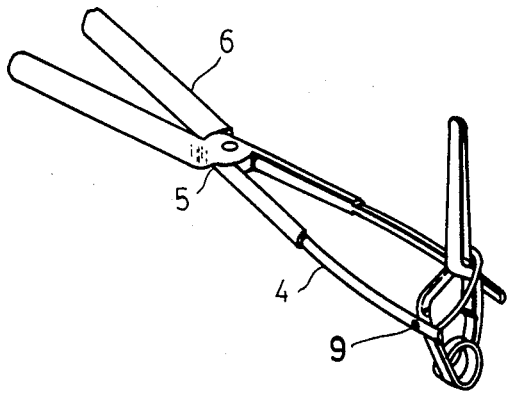
Figure 26:
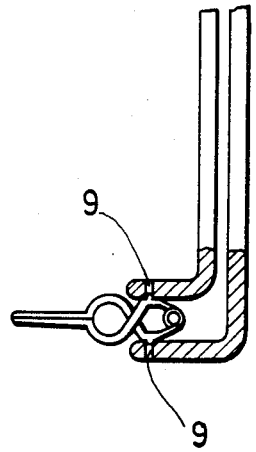
Figure 27:
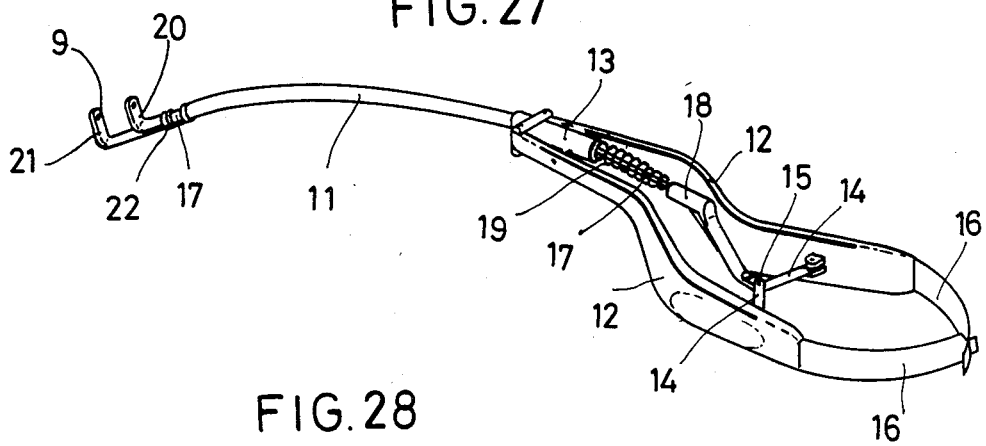
Figure 28:
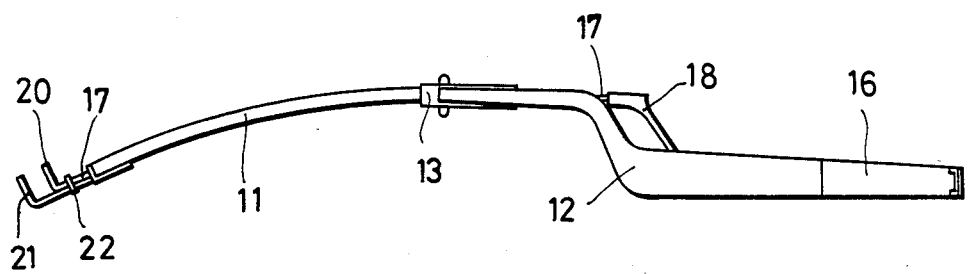
Figure 29:
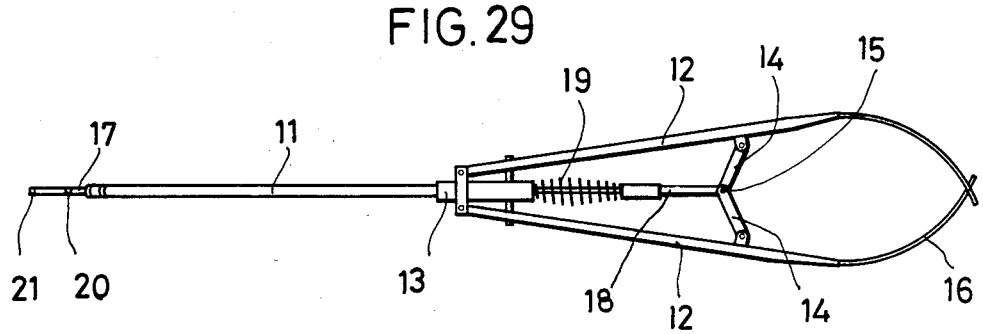
Figures 30, 31:
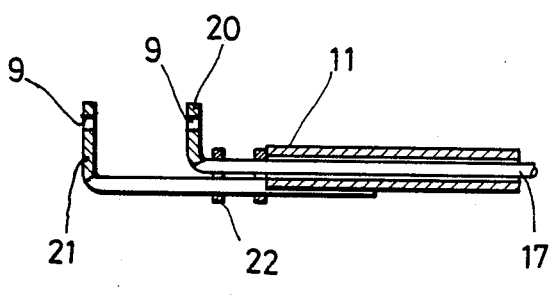

Figs . 8, 9 and 10 are perspective views of conventional forceps for clamping the clips;

FIGS. 11, 13 and 15 are perspective views thereof, with the clips clamped thereby;

FIGS. 12 and 14 are enlarged perspective views of parts of the forceps shown in FIGS. 11 and 13, respectively;

FIGS. 16, 18 and 20 are plan views of clips according to the present invention;

FIGS. 17, 19 and 21 are side views of the clips shown in FIGS. 16, 18 and 20, respectively;

FIG. 22 is a plan view of another clip according to the present invention;

FIG. 23 is a perspective view of the end portion of one half of forceps provided with a depression or a small hole according to the present invention;

FIG. 24 is a sectional view, illustrating a part of a clip with its projection fitted in the above-described small hole;

FIG. 25 is a perspective view of forceps clamping a clip according to the present invention;

FIG. 26 is a partially cutaway side view of forceps clamping a clip according to the present invention;

FIG. 27 is a perspective view of forceps according to the present invention;

FIG. 28 is a side view of forceps shown in FIG. 27;

FIG. 29 is a plan view of forceps shown in FIG. 27;

FIG. 30 is an enlarged sectional view of the end portion thereof; and

FIG. 31 is a side view of another type of the end portion thereof.

DETAILED DESCRIPTION OF THE PREFERRED EMBODIMENT

Figure 1:
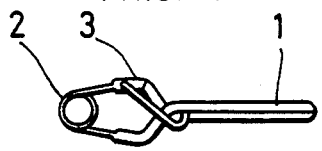
FIGS. 1, 3 and 5 are plan views of conventional surgical clips.
Figure 3:
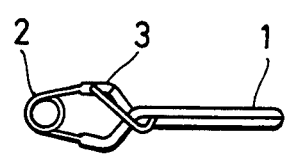
Figure 2:
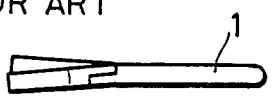
FIGS. 2, 4 and 6 are side views of the clips shown in FIGS. 1, 3 and 5, respectively.
Figure 4:
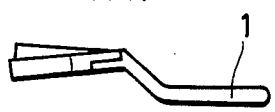
Figure 5:
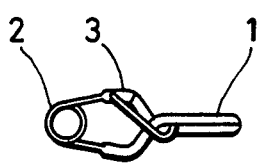
Figure 7:
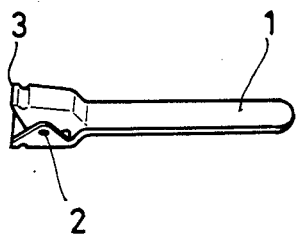
FIG. 7 is a perspective view of another conventional clip.
Figure 6:
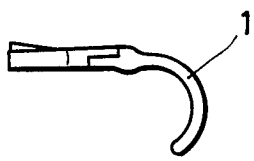

The clip in accordance with the present invention may take various shapes and dimensions irrespective as to whether a clamping jaw portion 1 and a load-bearing portion 3 are provided on the same side of a spring eye (or fulcrum) 2 as shown in FIGS. 1, 3 and 5 or on the opposite sides of the spring eye 2 as shown in FIG. 7. As shown in FIGS. 16 to 22, projections 3' are provided on the outer sides of the load-bearing portion. The projections 3' are not limited to a special shape but may be cylindrical, conical, hemispherical, or similarly shaped. In view of the specialty of the region where the clip is used, it is preferable to round the tip and edge of each projection 3' so as not to inflict an ijruy on the surrounding tissue. If the load-bearing portion 3 is broad as shown in FIG. 22, it is preferable to dispose each projection 3' at the broadwise middle point of the load-bearing portion 3 so that the clip may be stabilized when it is clamped by forceps.

In order to furnish a surgeon with a broad visual field within an incision, the holding portion of the forceps in accordance with the present invention consists of a pair of slender cylindrical rods made of a highly rigid material. The inside opposite surfaces of these rods should preferably be flat so as to stabilize the clip when it is clamped by the forceps or so as to allow it to smoothly swing. As shown in FIGS. 23 and 24, depressions or small holes 9 for receiving the projections 3' of the clip are provided in the end portions of the rods. The depressions or small holes 9 may be wholly or partially tapered. The clip can be securely clamped by the forceps if the diameter of the openings of the depressions or small holes 9 is equal to or slightly smaller than the diameter of the bases of the projections 3'. Conical or similarly shaped projections 3' can be especially easily fitted in the depressions or small holes 9. Small holes 9 of a through type instead of a blind type facilitate the postoperative cleaning and sterilization of the forceps.

Figure 9:
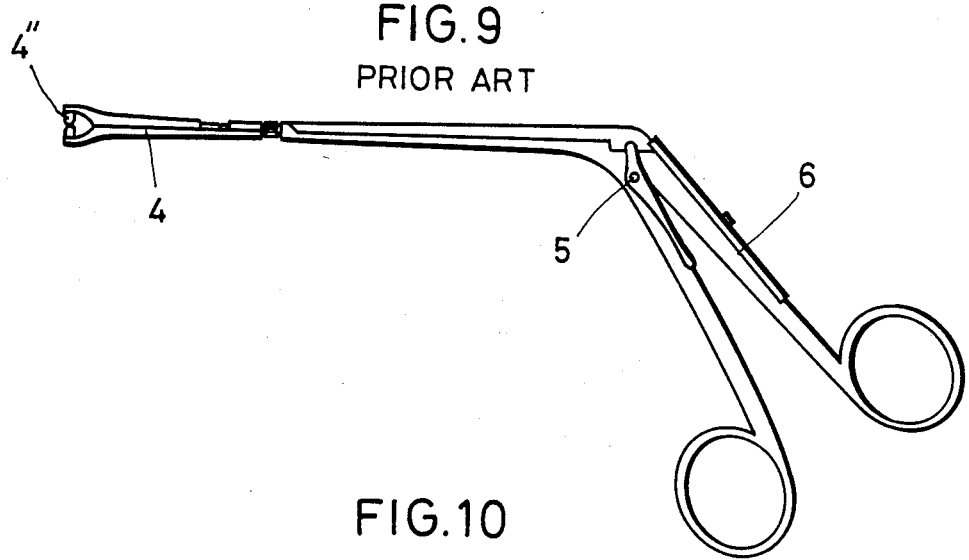

The forceps in accordance with the present invention are not limited to the X-shaped ones which are characterized in that the holding portion 4, connecting portion 5 and grip portion 6 are aligned with each other as shown in FIG. 25. The forceps may be, e.g., double L-shaped as shown in FIG. 26, or may be of a type in which one of the two jaws constituting the holding portion 4 is movable toward and away from the other as shown in FIG. 9 or both of them are movable toward and away from one another. No restrictions are imposed on the mechanism (structure, shape and dimensions) of the connecting portion 5 and the grip portion 6 of the forceps. The holding portion 4 per se may also take various shapes. Thus the forceps can be shaped in any manner by choosing a proper combination of the holding portion 4 and the grip portion 6.

Referring now to FIGS. 27 to 31, the forceps according to another embodiment of the present invention include a guide tube 11, which may be a rigid straight tube, a curved tube or a bent tube. In the alternative, the guide tube 11 may be a flexible tube which can be freely curved or bent to a certain extent and yet is capable of retaining its shape. No limitation is set about the material for the guide tube 11, except that it should be corrosion-resistant to the humidity, saline solution, etc.

A pair of control levers 12 is directly connected to one end of the guide tube 11 either hingedly or by welding. In the alternative, the end of the guide tube 11 is covered with a support tube 13 as shown in Figs. 27 to 29. The support tube 13 allows the guide tube 11 to rotate on its axis but prevents it from moving in the axial direction. The control levers 12 are connected to the support tube 13 either hingedly or by welding. This construction is a great convenience to the angular adjustment of the control levers 12 on the axis of the guide tube 11 even if the guide tube 11 is a highly rigid (poorly flexible) curved tube.

The control levers 12 are movable toward and away from one another and are connected with a pair of links 14, which are jointed together at a knee 15 so that, when force is applied to or retracted from the control levers 12 to move them toward or away from one another, the knee 15 is subjected to a motion in the axial direction of the guide tube 11. In order to allow the control levers 12 to easily move away from one another, a leaf spring 16 is provided on the end of each lever 12 as shown in FIGS. 27 to 29. In the alternative, the same purpose may be accomplished by a leaf spring or a coil spring (not shown) provided in the portion where the control levers 12 are connected with the guide tube 11 or the support tube 13. If the control levers 12 are provided with rings to be passed over a thumb and a forefinger as is the case with the grip portion 6 shown in FIG. 9, the use of the forceps will be restricted by the direction determined by the thumb and the forefinger. It is preferable, therefore, that the control levers 12 should bear resemblance to tweezers so as to be clasped by palms in all directions. Forceps provided with control levers 12 in which a step-shaped (bayonet-shaped) offset is formed as shown in FIG. 28 are also within the scope of the present invention.

The reciprocation of the knee 15 is transmitted to the tip of the guide tube 11 by means of a wire rod 17 extending therethrough. The wire rod 17 should preferably be flexible but incapable of axial expansion and contraction, and highly autitwisting and corrosion-resistant. The wire rod 17 is connected to the knee 15 either directly or indirectly depending upon whether the control levers 12 are formed with a step-shaped offset or not. Indirect connection is effected by the interposition of a coupler 18 as shown in FIGS. 27 to 29. The wire rod 17 may be connected to the coupler 18 in the same manner as the connection of the guide tube 11 to the support tube 13, i.e., in such a manner that the coupler 18 allows the wire rod 17 to rotate on its axis but prevents it from moving in the axial direction. A coil spring 19 may be interposed either between the support tube 13 and the knee 15 or between the support tube 13 and the coupler 18 as an auxiliary means for supplementing the tension of the leaf spring 16 and thereby allowing the control levers 12 to more easily move away from one another.

A movable clamping piece 20 is provided on the end of the wire rod 17 projecting from the end of the guide tube 11. A fixed clamping piece 21 is provided on the end of the guide tube 11. The movable clamping piece 20 may be formed integrally with the wire rod 17 by bending it, or may be separately formed and welded to the end of the wire rod 17. In either case, it is important that the movable clamping piece 20 should be in parallel with the fixed clamping piece 21 and both pieces should face each other. Preferably a guide ring 22 is provided to prevent the movable clamping piece 20 from being placed in a skew position relative to the fixed clamping 21.

Figure 8:
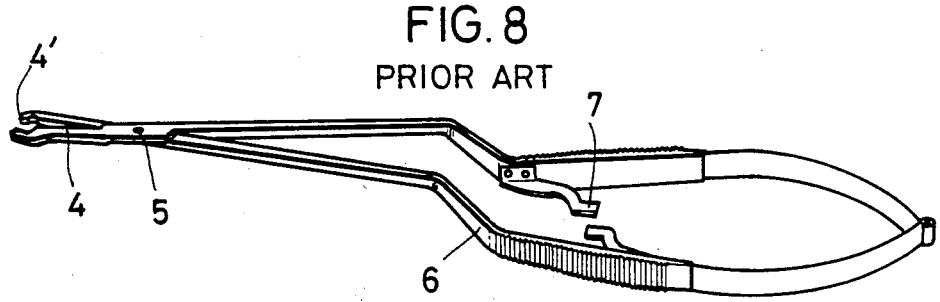
Figure 10:
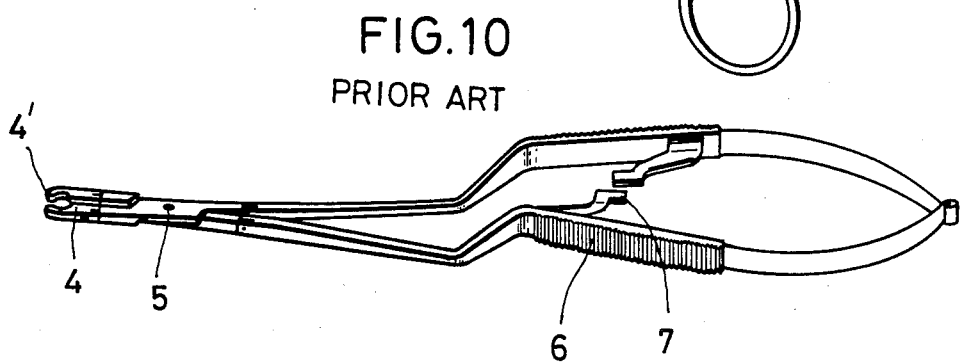

In order to stabilize the clip when it is clamped by the movable clamping piece 20 and the fixed clamping piece 21, both pieces have plane surfaces facing each other and are provided with depressions or small holes 9 for receiving the projections 3' of the clip. Seemingly, this arrangement makes the pieces 20 and 21 equivalent to the holding portion 4 of the conventional forceps shown in FIGS. 8 to 10. However, there is a wide structural difference therebetween in that, although the jaws constituting the holding portion 4 of the conventional forceps are moved on a pivot, the movable clamping piece 20 in accordance with the present invention is moved parallel to the fixed clamping piece 21.

When the control levers 12 are clasped by palms, the knee 15, together with the wire rod 17 connected thereto directly or indirectly, is pushed toward the end of the forceps. Thus, the movable clamping piece 20 is pushed toward the fixed clamping piece 21 so as to reduce the distance therebetween. However, if the knee 15 is disposed toward the leaf springs 16 (away from the guide tube 11) in contrast with the position of the knee 15 shown in FIGS. 27 to 29, the wire rod 17 will be drawn near when the control levers 12 are clasped. In this case, therefore, the position of the movable clamping piece 20 relative to the fixed clamping piece 21 shown in FIG. 30 must be inverted so as to dispose the fixed clamping piece 21 on the end of the guide tube 11 and the movable clamping piece 20 away therefrom as shown in FIG. 31. In either case, it is important that the movable clamping piece 20 should be in parallel with the fixed clamping piece 21 and both pieces should face each other. The above-described guide ring 22 shown in FIGS. 30 and 31 is a preferable means for conforming the clamping pieces to this requirement. Another preferable way is to allow the bore of the guide tube 11 to have the same section as the wire rod 17 in the form, e.g., of a circle, a portion of which is cut off so as to prevent the wire rod 17 from rotating on the axis of the guide tube 11. As mentioned above, the support tube 13 and the coupler 18 allow the guide tube 11 and the wire rod 17, respectively, to rotate on their axes without allowing them to move in the axial direction. Thus the guide tube 11 and the wire rod 17 can be rotated as a set on their axes so that the clamping pieces 20 and 21 may be directed in any sense with respect to the plane formed by the control levers 12. In order to allow the forceps in accordance with the present invention to be used for various purposes, the shapes of the guide tube 11 and the control levers 12 may be varied (for example, they may be of straight, curved or bent type) and the sense of the clamping pieces 20 and 21 with respect to the above-mentioned plane may also be varied.

Thus the forceps in accordance with the present invention can be utilized to clamp a conventional clip of any type on condition that projections 3' are provided on the outer sides of the load-bearing portion 3 of the clip. The angle of the clip on the axis of the guide tube 11 can be freely and easily changed as occasion demands. So far, surgeons have sometimes been confronted with inoperable cases even when they keep a sufficiently large number of variously shaped clips and forceps ready close to their hands. The present invention will not only obviate their having to be confronted with such cases, but also furnish them with a broad visual field within an incision, because the holding portion 4 of the forceps in accordance with the present invention is so simple in construction as to be space saving even when the clip is clamped thereby.

If the control levers 12 were provided with rings to be passed over a thumb and a forefinger, the use of the forceps would be restricted by the direction determined by the thumb and the forefinger. The forceps in accordance with the present invention are free from such directional restriction and can be used for easily and securely clamping an aneurism found on an artery running lengthwise in a field of operation regardless of the direction in which a surgeon is looking thereon.

What I claim is:
1. Forceps for holding a surgical clip provided with projections thereon, said forceps comprising:
   a guide tube having a longitudinal axis;
   a pair of control levers connected to one end of the guide tube so as to be movable toward and away from each other;
   a pair of links connected at one end to the pair of control levers;
   knee means, connected to opposite ends of the pair of links, for joining the pair of links together;
   a wire rod extending through the guide tube and having one end connected to the knee means;
   a movable clamping piece being connected to an opposite end of the wire rod and projecting from an opposite end of the guide tube;
   a fixed clamping piece provided on the opposite end of the guide tube in parallel with the movable clamping piece; and
   bore means, provided in alignment with each other in the movable clamping piece and in the fixed clamping piece in a direction parallel with the longitudinal axis of the guide tube, for receiving projections provided on a surgical clip;
   whereby the surgical clip is clamped in a direction perpendicular to the longitudinal axis of the guide tube.

* * * * *